United States Patent
Yee et al.

(12) 
(10) Patent No.: US 6,420,525 B1
(45) Date of Patent: *Jul. 16, 2002

(54) HUMAN TRANSCRIPTION FACTOR ZGCL-1

(75) Inventors: David P. Yee; Theresa A. Deisher, both of Seattle, WA (US)

(73) Assignee: ZymoGenetics, Inc., Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/137,223

(22) Filed: Aug. 19, 1998

Related U.S. Application Data

(60) Provisional application No. 60/056,130, filed on Aug. 19, 1997.

(51) Int. Cl.[7] .............................................. C07K 14/47
(52) U.S. Cl. ...................................................... 530/350
(58) Field of Search ................................ 530/350, 358; 514/2; 435/375, 69.1, 191.4

(56) References Cited

FOREIGN PATENT DOCUMENTS

| WO | 99/27091 | | 6/1999 |
|---|---|---|---|
| WO | WO 99/27901 | * | 6/1999 |

OTHER PUBLICATIONS

Jongens et al. 1992. Cell 70:569–584.*
Chen et al. 1995. Molecular and Cellular Biology 15:3424–3429.*
Langer, R. Delivery and Targeting, Nature Suppl. 392, p5–10, Apr. 30, 1998.*
Jongens et al., Cell 70: 569–584, 1992.
Affara et al.,Genomics 22: 205–210, 1994.
Adams et al., TIGR EST 1997, AA348897.
Lee et al., Rat Genome Project, 1995, AA848792.
LifeSeq™ Clone Information Results, Incyte Phamaceuticals, 1995, Inc 305172.
LifeSeq™ Library Information Results, Incyte Phamaceuticals, 1995, HEARNOT01.
Marra, The Wash–U–HHMI Mouse EST Project, 1996, AA027445.
Marra, The Wash–U–HHMI Mouse EST Project, 1996, AA048295.
LifeSeq™ Clone Information Results, Incyte Phamaceuticals, 1996, INC 2352423.
LifeSeq™ Library Information Results, Incyte Phamaceuticals. 1996, COLSUCT01.
LifeSeq™ Clone information Results, Incyte Phamaceuticals, 1997, INC2566060.
LifeSeq™ Clone Information Results, Incyte Phamaceuticals, 1997, INC3341327.
LifeSeq™ Clone Information Results, Incyte Phamaceuticals, 1997, INC3533365.
LifeSeq™ Clone Information Results, Incyte Phamaceuticals, 1998, Inc4349238.
LifeSeq™ Library Information Results, Incyte Phamaceuticals, 1998, TLYMTX01.
LifeSeq™ Library Information Results, Incyte Phamaceuticals, 1997, THYMNOT04.
LifeSeq™ Library Information Results, Incyte Phamaceuticals, 1998, SPLNNOT099.
LifeSeq™ Library Information Results, Incyte Phamaceuticals, 1998, KIDNNOT25.
Nakamura et al, J. Gen Virol. 75: 2625–2633, 1994.

* cited by examiner

*Primary Examiner*—Terry McKelvey
(74) *Attorney, Agent, or Firm*—Susan E. Lingenfelter

(57) ABSTRACT

Novel ZGCL-1 transcription factor polypeptides, polynucleotides encoding the polypeptides, and related compositions and methods are disclosed. The polypeptides, agonists and antagonists may be used within methods for promoting the proliferation and/or differentiation of testis cells, and may also be used in the development of male-specific contraceptives and infertility treatments.

2 Claims, 2 Drawing Sheets

```
           10         20         30         40         50         60
zgc11 MRRATDSVTVRGSHKRKRSSGSFCYCHPDSETDEDEEEGDEQQRLLNTPRRKKLKSTSKY
      :::.   .  :    :     . :.....:::  ::..:
GCL1D    MGQIVGSMHMNVAEVFSNRRKRKRSTDSSLGKDDPAQLDTTQPKKKKLLTTTQY
              10         20         30         40         50

70         80         90        100        110        120
zgc11 IYQTLFLNGENSDIKICALGEEWSLHKIYLCQSGYFSSMFSGSWKESSMNIIELEIPDQN
      ::..:  .:::. .  :  :: :.:::..::  :::::::::::::::::  .  : ...
GCL1D IYKALFKEEKNSDVAVMALDKVWHLHKVYLSQSPYFYTMFNGTWREAQQNFIQITILDDR
         60         70         80         90        100        110

130        140        150        160        170        180
zgc11 IDVEALQVAFGSLYRDDVLIKPSRVVAILAAACLLQLDGLIQQCGETMKETVNVKTVCGY
      : :  .:.......::  :.  ::  .  :......:  :...:.::::.  ...  .. :
GCL1D ITVASLDAVFGSMYSDEIEIESADVISVLATATLFHLDGIIDKCAEVMVDNISPETAIQY
         120        130        140        150        160        170

190        200        210        220        230
zgc11 YTSAGTYGLDSVKKKCLEWLLNNLMT--HQNVELFKELSINVMKQLIGSSNLFVMQVEMD
      :  .:   .:::.   .::::.  .::: ..  :::::::::::.   : ..: ..:.:::::
GCL1D YEAACQYGVVGVKKSTFQWFQINLLSIYSKQPNLLRHISIELMSALTASPDLYVMQTEFS
         180        190        200        210        220        230

240        250             260        270
zgc11 IYTALKKWMFLQLVPSWNGS----------LKQLLTETDVWFSKQRKDF----------E
      .:: :: :.:::::: :    .        .:::::::   :       :
GCL1D LYTLLRTWMFLRLHPDYDPEDPVQRAEALKTQELLVNAGVETHAPSGDVVQWTYFTSRSE
         240        250        260        270        280        290

280        290        300        310        320        330
zgc11 GMAFLETEQGKPFVSVFRHLRLQYIISDLASARIIEQDAVVPSEWLSSVYKQQWFAMLRA
      .:: : .:.:::::. :: ::. .   . :::. .: .:::.:::::  ::: :..::.:::
GCL1D ERSFLATPEGQPYVKVFQKLRTQYLTNHYMDLKIIYNDNIIPKEWLYRHIHNHWDALLRI
         300        310        320        330        340        350
```

Fig. 1a

```
              340        350        360        370        380        390
zgcl1  EQDSE-VGPQEINKEELEGNSMRCGRKLAKDGEYCWRWTGFNFGFDLLVTYTNRYIIFKR
        ..  .:  .::... :..   :  :::::  :    :    :::::::::::::..   .:  . ...:
GCL1D  DHGQEDCSPQQLDDEQFFENCMRCGRMLLEPGYQKWRWTGFNFGMDLILIMDSRRLNIRR
              360        370        380        390        400        410

400        410        420        430        440        450
zgcl1  NTLNQPCSGSVSLQPRRSIAFRLRLASFDSSGKLICSRTTGYQILTLEKDQEQVVMNLDS
        .  ..  .  .:::  ...     :  ..:.....  .  ...:        :.:::...:  .:  ::
GCL1D  HHRHEH-ERVLSLQTKRKFMVRTTVTSINAQRQAVFTQTSEICSLSLEKNEEVPLMVLDP
              420        430        440        450        460        470

460        470
zgcl1  RLLIFPLYICCNFLYISPEKKN
        .:  .  :: .:  ...  :  .  ...
GCL1D  KL-VHPLLISINMLVVMPPNQSFKEIVPLSEEATTSLSIPISEIGANSDRPLSPSSADDS
              480        490        500        510        520        530

GCL1D  AVFIGDSEPSTP
              540
```

Fig. 1b

HUMAN TRANSCRIPTION FACTOR ZGCL-1

REFERENCE TO RELATED APPLICATIONS

This application claims the benefit of U.S. Provisional Application No. 60/056,130, filed Aug. 19, 1997.

BACKGROUND OF THE INVENTION

Proliferation and differentiation of cells of multicellular organisms are controlled by hormones and polypeptide growth factors. These diffusable molecules allow cells to communicate with each other and act in concert to form cells and organs, and to repair and regenerate damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the transcription factors.

Transcription factors regulate the transcription of genes in the cell by interacting with other transcription factors and RNA polymerase. Transcription factors are characterized by their DNA-binding domain and their transcriptional activation domain. Within the DNA binding domain, several different motifs have been identified which act to mediate DNA binding to transcription factors. These include cysteine-histidine zinc finger and multi-cysteine zinc finger motifs, homeobox motifs, winged helix motifs, leucine-zipper motifs, and helix-loop-helix motifs. The activation domain can contain a large number of acetic amino acids which form an amphipathic α-helix with its negative charges displayed on one surface. Others have glutamine or proline-rich regions.

Following DNA binding, the transcription factor interacts with other factors or the RNA polymerase to stimulate transcription. Transcription can be blocked by molecules which are able to bind to the DNA binding domain but do not interact with the transcription domain. These repressor molecules prevent positively acting DNA molecules from binding.

The location of the transcription factors bound by a particular gene control the gene's expression pattern. If a gene binds a transcription factor which is ubiquitously expressed, then the gene expression will be as well. If the gene binds a transcription factor which is synthesized or active only in a limited number of cells, gene expression will be more cell specific. Regulation of gene expression is for the most part controlled by transcription factors. This regulation provides that the correct gene is activated in the appropriate cell at the precise time for development. Identification of transcription factors and the genes they regulate greatly enhances our understanding of cellular development. As a result intervention methods can be developed to alleviate problems associated with transcription. The present invention addresses this need by providing a novel transcription factor and related compositions and methods.

SUMMARY OF THE INVENTION

The present invention provides a novel testis specific transcription factor and related compositions and methods.

Within one aspect is provided an isolated polypeptide comprising a sequence of amino acid residues that is at least 80% identical in amino acid sequence to residues 1–479 of SEQ ID NO:2, wherein the sequence comprises a POZ domain corresponding to amino acid residues 61–178 of SEQ ID NO:2. Within one embodiment the polypeptide is at least 90% identical in amino acid sequence to residues 1–479 of SEQ ID NO:2, wherein the sequence comprises a POZ domain corresponding to amino acid residues 61–178 of SEQ ID NO:2. Within another embodiment the polypeptide is covalently linked amino terminally or carboxy terminally to a moiety selected from the group consisting of affinity tags, toxins, radionucleotides, enzymes and fluorophores.

Within another aspect is provided an isolated polynucleotide encoding a polypeptide comprising a sequence of amino acid residues that is at least 80% identical in amino acid sequence to residues 1–479 of SEQ ID NO:2, wherein the sequence comprises a POZ domain corresponding to amino acid residues 61–178 of SEQ ID NO:2. Within one embodiment the polypeptide is at least 90% identical in amino acid sequence to residues 1–479 of SEQ ID NO:2, wherein said sequence comprises a POZ domain corresponding to amino acid residues 61–178 of SEQ ID NO:2.

Within another aspect the polynucleotide comprising the sequence of nucleotide 1 to nucleotide 1437 of SEQ ID NO:4.

Within yet another aspect is provided an oligonucleotide probe or primer comprising at least 14 contiguous nucleotides of a polynucleotide of SEQ ID NO:4 or a sequence complementary to SEQ ID NO:4.

Also provided by the invention is an expression vector comprising the following operably linked elements: a transcription promoter; a DNA segment encoding a polypeptide comprising a sequence of amino acid residues that is at least 80% identical in amino acid sequence to residues 1–479 of SEQ ID NO:2, wherein the sequence comprises a POZ domain corresponding to amino acid residues 61–178 of SEQ ID NO:2; and a transcription terminator. Within one embodiment the DNA segment encodes a polypeptide that is at least 90% identical in amino acid sequence to residues 1–479 of SEQ ID NO:2, wherein the sequence comprises a POZ domain corresponding to amino acid residues 61–178 of SEQ ID NO:2. Within another embodiment the DNA segment encodes a polypeptide covalently linked amino terminally or carboxy terminally to an affinity tag. Within still another embodiment the DNA segment further encodes a secretory signal sequence operably linked to the polypeptide.

Within another aspect is provided a cultured cell into which has been introduced an expression vector comprising the following operably linked elements: a transcription promoter; a DNA segment encoding a polypeptide comprising a sequence of amino acid residues that is at least 80% identical in amino acid sequence to residues 1–479 of SEQ ID NO:2, wherein the sequence comprises a POZ domain corresponding to amino acid residues 61–178 of SEQ ID NO:2; and a transcription terminator; wherein the cell expresses the polypeptide encoded by the DNA segment.

Within another aspect is method of producing a polypeptide comprising: culturing a cell into which has been introduced an expression vector comprising the following operably linked elements: a transcription promoter; a DNA segment encoding a polypeptide comprising a sequence of amino acid residues that is at least 80% identical in amino acid sequence to residues 1–479 of SEQ ID NO:2, wherein the sequence comprises a POZ domain corresponding to amino acid residues 61–178 of SEQ ID NO:2; and a transcription terminator; whereby the cell expresses the polypeptide encoded by the DNA segment; and recovering the expressed polypeptide.

Another aspect provided herein is a pharmaceutical composition comprising a polypeptide, the polypeptide comprising a sequence of amino acid residues that is at least 80 identical in amino acid sequence to residues 1–479 of SEQ ID NO:2, wherein the sequence comprises a POZ domain corresponding to amino acid residues 61–178 of SEQ ID NO:2; in combination with a pharmaceutically acceptable vehicle.

Within another aspect is an antibody that specifically binds to an epitope of a polypeptide comprising a sequence of amino acid residues that is at least 80% identical in amino acid sequence to residues 1–479 of SEQ ID NO:2, wherein the sequence comprises a POZ domain corresponding to amino acid residues 61–178 of SEQ ID NO:2.

Also provided is a binding protein that specifically binds to an epitope of a polypeptide comprising a sequence of amino acid residues that is at least 80% identical in amino acid sequence to residues 1–479 of SEQ ID NO:2, wherein the sequence comprises a POZ domain corresponding to amino acid residues 61–178 of SEQ ID NO:2.

Also provided is a method for detecting a genetic abnormality in a patient, comprising: obtaining a genetic sample from a patient; incubating the genetic sample with a polynucleotide comprising at least 14 contiguous nucleotides of SEQ ID NO:1 or the complement of SEQ ID NO:1, under conditions wherein the polynucleotide will hybridize to complementary polynucleotide sequence, to produce a first reaction product; comparing the first reaction product to a control reaction product, wherein a difference between the first reaction product and the control reaction product is indicative of a genetic abnormality in the patient.

These and other aspects of the invention will become evident upon reference to the following detailed description and the attached drawing.

BRIEF DESCRIPTION OF THE DRAWING

FIGS. 1A–1B show a comparison of the deduced amino acid sequence of ZGCL-1 (SEQ ID NO:2) with the deduced amino acid sequence of the Drosophila gene germ cell-less (dGCL-1) (SEQ ID NO:3).

DETAILED DESCRIPTION OF THE INVENTION

Prior to setting forth the invention, it may be helpful to an understanding thereof to set forth definitions of certain terms to be used hereinafter:

Affinity tag: is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

Allelic variant: Any of two or more alternative forms of a gene occupying the same chromosomal locus. Allelic variation arises naturally through mutation, and may result in phenotypic polymorphism within populations. Gene mutations can be silent (i.e., no change in the encoded polypeptide), or may encode polypeptides having altered amino acid sequence. The term "allelic variant" is also used herein to denote a protein encoded by an allelic variant of a gene. Also included are the same protein from the same species which differs from a reference amino acid sequence due to allelic variation. Allelic variation refers to naturally occurring differences among individuals in genes encoding a given protein.

Amino-terminal and carboxyl-terminal: are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

Complement/anti-complement pair: Denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^{-9}$ M.

Complements of polynucleotide molecules: Denotes polynucleotide molecules having a complementary base sequence and reverse orientation as compared to a reference sequence. For example, the sequence 5' ATGCACGGG 3' is complementary to 5' CCCGTGCAT 3'.

Contig: Denotes a polynucleotide, a segment of which is equivalent in nucleotide sequence to a segment of another polynucleotide sequence. A "contig assembly" denotes a collection of EST contigs that define a larger polynucleotide segment containing an open reading frame encoding a full-length or partial polypeptide.

Degenerate: As applied to a nucleotide sequence such as a probe or primer, denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

Expression vector: A DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Isolated: when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

Isolated polypeptide or protein: is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

Operably linked: As applied to nucleotide segments, the term "operably linked" indicates that the segments are arranged so that they function in concert for their intended purposes, e.g., transcription initiates in the promoter and proceeds through the coding segment to the terminator.

Ortholog: denotes a polypeptide or protein obtained from one species that is the functional counterpart of a polypeptide or protein from a different species. Sequence differences among orthologs are the result of speciation.

Paralogs: are distinct but structurally related proteins made by an organism. Paralogs are believed to arise through gene duplication. For example, α-globin, β-globin, and myoglobin are paralogs of each other.

Polvnucleotide: is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

Polypeptide: is a polymer of amino acid residues joined by peptide bonds, whether produced naturally or synthetically. Polypeptides of less than about 10 amino acid residues are commonly referred to as "peptides".

Promoter: Denotes a portion of a gene containing DNA sequences that provide for the binding of RNA polymerase and initiation of transcription. Promoter sequences are commonly, but not always, found in the 5' non-coding regions of genes.

Protein: is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

Receptor: A cell-associated protein, or a polypeptide subunit of such protein, that binds to a bioactive molecule (the "ligand") and mediates the effect of the ligand on the cell. Binding of ligand to receptor results in a change in the receptor (and, in some cases, receptor multimerization, i.e., association of identical or different receptor subunits) that causes interactions between the effector domain(s) of the receptor and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

Secretory signal sequence: A DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

Soluble receptor or ligand: A receptor or a ligand polypeptide that is not bound to a cell membrane. Soluble receptors are most commonly ligand-binding receptor polypeptides that lack transmembrane and cytoplasmic domains. Soluble ligands are most commonly receptor-binding polypeptides that lack transmembrane and cytoplasmic domains. Soluble receptors or ligands can comprise additional amino acid residues, such as affinity tags that provide for purification of the polypeptide or provide sites for attachment of the polypeptide to a substrate. Many cell-surface receptors and ligands have naturally occurring, soluble counterparts that are produced by proteolysis or translated from alternatively spliced mRNAs. Receptor and ligand polypeptides are said to be substantially free of transmembrane and intracellular polypeptide segments when they lack sufficient portions of these segments to provide membrane anchoring or signal transduction, respectively.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence (SEQ ID NO:1) and corresponding polypeptide sequence (SEQ ID NO:2) which have homology to the Drosophila gene "germ cell-less" (Jongens et al., *Cell* 70:569–584, 1992). Analysis of the tissue distribution of the mRNA corresponding to this novel DNA showed selective expression in the testes, suggesting that the ligand mediates processes of progenitor cell growth and development, such as spermatogenesis, that are unique to the testes. The ligand has been designated ZGCL-1.

Novel ZGCL-1 polynucleotides and polypeptides of the present invention were initially identified by querying an expressed sequence tag (EST) database. Using this information, a novel 1469 bp human cDNA fragment (SEQ ID NO:1) was obtained. Sequence analysis of a deduced amino acid sequence of ZGCL-1, as represented by SEQ ID NO:2, indicates the presence of a potential N-glycosylation site at amino acid residues 256–259 of SEQ ID NO: 2, as predicted by the PROSITE motif "ASN-GLYCOSYLATION". ZGCL-1 also contains 4 potential cAMP- and cGMP-dependent protein kinase phosphorylation sites at amino acid residues 2–5, 16–19, 17–20, and 396–399 of SEQ ID NO:2, as predicted by the PROSITE motif "CAMP-PHOSPHO-SITE". ZGCL-1 contains 5 potential protein kinase C phosphorylation sites as predicted by the PROSITE motif "PKC-PHOSPHO-SITE" at amino acid residues 9–11, 13–15, 48–50, 57–59, and 103–105 of SEQ ID NO:2. The proteins of the present invention comprise a sequence of amino acid residues that is at least 80% identical to SEQ ID NO:2. Within certain embodiments of the invention, the sequence is at least 90% or 95% identical to SEQ ID NO:2.

ZGCL-1 also contains a POZ domain, also referred to as the ZIN, BTB, or BR-C/TTK domain (Chen et al., *Mol. Cell. Biol.* 15:3424–39, 1995; Dong et al., *Proc. Natl. Acad. Sci. USA* 93:3624–29, 1996; Albagli et al., *Biochem. Biophys. Res. Comm.* 220:911–15, 1996; Chang et al., *Proc. Natl. Acad. Sci. USA* 93:6947–52, 1996 and Kaplan and Calame, *Nucleic Acid Research* 25:1108–16, 1997). This domain is located approximately between amino acid residues 61–178 of SEQ ID NO:2. The POZ domain is found in a number of Zinc finger containing proteins, in Drosophila, POZ domain are found in Tramtrack (Harrison and Travers, *EMBO J.* 9:207–16, 1990), Broad-complex (DiBello et al., *Genetics* 129:385–97, 1991), and Kelch (Xue and Cooley, *Cell* 72:681–93, 1993). The first two genes are developmental regulators, while the last gene codes for an actin binding protein. POZ is also found in POX virus genes such as Myxoma virus MAP1 (Upton et al., *Virology* 179:618–31, 1990) and vaccinia virus protein a55 (Genbank accession # P24768). POZ is also found in a few human genes: KUP (Chardin et al., *Nucleic Acid Research* 19:1431–36, 1991), ZID (Bardwell and Treisman, *Genes Dev.* 8:1664–77, 1994), and PLZF (Chen et al., *EMBO J.* 12:1161–67, 1993). POZ domains are thought to mediate protein-protein interactions. Most of the characterized POZ domains form homomeric interactions, though there are a few examples of POZ domains that form heteromeric interactions (Ttk and GAGA). The POZ domain is associated with transcriptional regulators and proteins that contain DNA binding Zinc fingers, however there are some examples of non-zinc-finger POZ domain proteins, such as Kelch. Like Kelch, ZGCL-1 does not contain any zinc-finger motifs and interestingly Kelch is involved in oogenesis. Those skilled in the art will recognize that these domain boundaries are approximate, and are based on alignments with known proteins and predictions of protein folding.

A comparison of the ZGCL-1 deduced amino acid sequence (as represented in SEQ ID NO:2) with the deduced amino acid sequence of Drosophila germ cell-less gene (SEQ ID NO:13) is shown in the Figure. ZGCL-1 shares 35% amino acid identity with the Drosophila "germ cell-less" gene (Jongens et al., *Cell* 70:569–84, 1992). The DNA sequence as represented by SEQ ID NO:1 is considered to be the human homolog of the Drosophila "germ cell-less" gene.

Northern blot analysis of various human tissues was performed using a 200 bp DNA probe (SEQ ID NO:3). A 3.2 kb transcript was detected corresponding to ZGCL-1. A high level of transcription was detected in testis and a lower level of transcription was detected in thyroid, spinal cord, stomach, lymph node and trachea. A second transcript of 4.5 kb, corresponding to a low level of transcription in placenta and pancreas, was also detected.

Radiation hybrid mapping is a somatic cell genetic technique developed for constructing high-resolution, contiguous maps of mammalian chromosomes (Cox et al., *Science* 250:245–250, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other nonpolymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

Chromosomal localization of ZGCL-1 to 5q35.3 was determined using radiation hybrid chimeras. Human 5q34–q35 genes have been primarily localized to mouse chromosome 11, in the A5-B1 and A1-B1 region. The mouse "germ cell deficient" gene, GCD, locus maps to chromosome 11 in the A2-A3 region (Duncan et al., *Mamm. Genome* 6:697–9, 1995). Germ cell deficient leads to improper migration and/or proliferation of primordial germ cells during embryonic development resulting in infertility in the adult mouse. Mice having this mutation have been hypothesized to be animal models for the human reproductive disorders, premature ovarian failure and Sertoli cell only syndrome.

Polynucleotide sequences encoding highly conserved amino acids or amino acid domains of ZGCL-1 can be used as a tool to identify new family members. For instance, reverse transcription-polymerase chain reaction (RT-PCR) can be used to amplify sequences encoding domains or conserved regions, described above and shown in the Figure, from RNA obtained from a variety of tissue sources or cell lines. In particular, highly degenerate primers designed from the ZGCL-1 sequences are useful for this purpose.

The present invention also provides polynucleotide molecules, including DNA and RNA molecules, that encode the ZGCL-1 polypeptides disclosed herein. Those skilled in the art will readily recognize that, in view of the degeneracy of the genetic code, considerable sequence variation is possible among these polynucleotide molecules. SEQ ID NO:4 is a degenerate DNA sequence that encompasses all DNAs that encode the ZGCL-1 polypeptide of SEQ ID NO:2. Those skilled in the art will recognize that the degenerate sequence of SEQ ID NO:4 also provides all RNA sequences encoding SEQ ID NO:2 by substituting U (uracil) for T (thymine). Thus, ZGCL-1 polypeptide-encoding polynucleotides comprising nucleotide 1 to nucleotide 1437 of SEQ ID NO:4 and their RNA equivalents are contemplated by the present invention. Table 1 sets forth the one-letter codes used within SEQ ID NO:4 to denote degenerate nucleotide positions. "Resolutions" are the nucleotides denoted by a code letter. "Complement" indicates the code for the complementary nucleotide(s). For example, the code Y denotes either C (cysteine) or T, and its complement R denotes A (adenosine) or G (guanine), A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, encompassing all possible codons for a given amino acid, are set forth in Table 2.

TABLE 2

| Amino Acid | One Letter Code | Condons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | ... | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention, isolated polynucleotides will hybridize to similar sized regions of SEQ ID NO:1, or to a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C. As previously noted, the isolated polynucleotides of the present invention include DNA and RNA. Methods for isolating DNA and RNA are well known in the art. It is generally preferred to isolate RNA from testis although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. Polynucleotides encoding ZGCL-1 polypeptides are then identified and isolated by, for example, hybridization or PCR.

Those skilled in the art will recognize that the sequence disclosed in SEQ ID NO:1 represents a single allele of the human ZGCL-1 gene, and that allelic variation and alternative splicing, "splice variants", are expected to exist. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. Splice variant is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. cDNAs generated from alternatively spliced mRNAs, which retain the properties of the ZGCL-1 polypeptide are included within the scope to the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention further provides counterpart ligands and polynucleotides from other species (orthologs). These orthologous polynucleotides can by used, inter alia, to prepare the respective orthologous proteins. These species would include, but are not limited to, mammalian, avian, amphibian, reptile, fish, insect and other vertebrate and invertebrate species. Of particular interest are ZGCL-1 ligand polypeptides from other mammalian species, including murine, porcine, ovine, bovine, canine, feline, equine, and other primate ligands. Orthologs of human ZGCL-1 can be cloned using information and compositions provided by the present invention in combination with conventional cloning techniques. For example, a cDNA can be cloned using mRNA obtained from a tissue or cell type that expresses the ligand. Suitable sources of mRNA can be identified by probing Northern blots with probes designed from the sequences disclosed herein. A library is then prepared from mRNA of a positive tissue or cell line. A ZGCL-1-encoding cDNA can then be isolated by a variety of methods, such as by probing with a complete or partial human cDNA or with one or more sets of degenerate probes based on the disclosed sequence. A cDNA can also be cloned using the polymerase chain reaction (PCR) (Mullis, U.S. Pat. No. 4,683,202), using primers designed from the sequences disclosed herein. Within an additional method, the cDNA library can be used to transform or transfect host cells, and expression of the cDNA of interest can be detected with an antibody to ZGCL-1. Similar techniques can also be applied to the isolation of genomic clones.

The present invention also provides isolated ligand polypeptides that are substantially homologous to the ligand polypeptide of SEQ ID NO:2 and its species orthologs. By "isolated" is meant a protein or polypeptide that is found in a condition other than its native environment, such as apart from blood and animal tissue. In a preferred form, the isolated protein or polypeptide is substantially free of other proteins or polypeptides, particularly other proteins or polypeptides of animal origin. It is preferred to provide the proteins or polypeptides in a highly purified form, i.e. greater than 95% pure, more preferably greater than 99% pure. The term "substantially homologous" is used herein to denote proteins or polypeptides having 50%, preferably 60%, more preferably at least 80%, sequence identity to the sequence shown in SEQ ID NO:2 or its species orthologs. Such proteins or polypeptides will more preferably be at least 90% identical, and most preferably 95% or more identical to SEQ ID NO:2 or its species orthologs. Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{\text{[length of the longer sequence plus the number of gaps introduced into the longer sequence in order to align the two sequences]}} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -3 | -3 | -1 | -2 | -4 | 7 | | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification, an affinity tag. Polypeptides comprising affinity tags can further comprise a proteolytic cleavage site between the ZGCL-1 polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethyl-cysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural mino acids may be substituted for ZGCL-1 amino acid esidues.

Essential amino acids in the polypeptides of he present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related "germ cell-less" proteins.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) nd region-directed mutagenesis (Derbyshire et al., *Gene* 6:145, 1986; Ner et al., *DNA* 7:127, 1988).

Variants of the disclosed ZGCL-1 DNA and olypeptide sequences can be generated through DNA huffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput screening methods to detect activity of cloned, mutagenized ligands. Mutagenized DNA molecules that encode active ligands or portions thereof (e.g., receptor-binding fragments) can be recovered from the host cells and rapidly sequenced using modern equipment.

These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to SEQ ID NO:2 or allelic variants thereof and retain the transcription mediating properties of the wild-type protein. Such polypeptides may include affinity tags and the like. Such polypeptides may also include additional polypeptide segments as generally disclosed above.

The ZGCL-1 polypeptides of the present invention, including full-length polypeptides, fragments (e.g., DNA-binding fragments), and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual, Second Edition*, Cold Spring Harbor, N.Y., 1989; and Ausubel et al., eds., *Current Protocols in Molecular Biology*, John Wiley and Sons, Inc., N.Y., 1987.

In general, a DNA sequence encoding a ZGCL-1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a ZGCL-1 polypeptide into the secretory pathway of a host cell, a secretory signal sequence (also known as a signal sequence, leader sequence, prepro sequence or pre sequence) is provided in the expression vector. The secretory signal sequence may be that of the ZGCL-1 polypeptide, or may be derived from another secreted protein (e.g., t-PA) or synthesized de novo. The secretory signal sequence is joined to the ZGCL-1 DNA sequence in the correct reading frame. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J*. 1:841–45, 1982), DEAE-dextran mediated transfection (Ausubel et al., ibid), and liposome-mediated transfection (Hawley-Nelson et al., *Focus* 15:73, 1993; Ciccarone et al., *Focus* 15 15:80, 1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al.,*J. Gen. Virol*. 36:59–72, 1977) and Chinese hamster ovary (e.g., CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601, 978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant ZGCL-1 baculovirus utilizes a transposon-based system described by Luckow (Luckow et al., *J Virol* 67:4566–79, 1993). This system, which utilizes transfer vectors, is sold in the Bac-to-Bac™ kit (Life Technologies, Rockville, Md.). This system utilizes a transfer vector, pFastBacl™ (Life Technologies) containing a Tn7 transposon to move the DNA encoding the ZGCL-1 polypeptide into a baculovirus genome maintained in *E. coli* as a large plasmid called a "bacmid." See, Hill-Perkins and Possee, *J. Gen. Virol.* 15 71:971–6, 1990; Bonning et al., *J. Gen. Virol.* 75:1551–6, 1994; and, Chazenbalk and Rapoport., *J. Biol. Chem.* 270:1543–9, 1995. In addition, transfer vectors can include an in-frame fusion with DNA encoding an epitope tag at the C- or N-terminus of the expressed ZGCL-1 polypeptide, for example, a Glu—Glu epitope tag (Grussenmeyer et al., *Proc. Natl. Acad. Sci.* 82:7952–4, 1985). Using a technique known in the art, a transfer vector containing ZGCL-1 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses ZGCL-1 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. Procedures used are generally described in available laboratory manuals (King and Possee, ibid.; O'Reilly et al., ibid.; Richardson, ibid.). Subsequent purification of the ZGCL-1 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a ZGCL-1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Expressed recombinant ZGCL-1 polypeptides (or chimeric ZGCL-1 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their physical properties. For example, immobilized metal ion adsorption (IMAC) chromatography can be used to purify histidine-rich proteins and those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., Glu—Glu affinity tag, FLAG tag, maltose-binding protein, an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

ZGCL-1 polypeptides or fragments thereof may also be prepared through chemical synthesis. ZGCL-1 polypeptides may be monomers or multimers; glycosylated or non-glycosylated; pegylated or non-pegylated; and may or may not include an initial methionine amino acid residue.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on and off-rates, from which binding affinity can be calculated, and assessment of stoichiometry of binding.

In vitro and in vivo response to ZGCL-1 can also be measured using cultured cells or by administering molecules of the claimed invention to the appropriate animal model. For instance, ZGCL-1 transfected expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vi tro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5 \times 10^5$ to about $5 \times 10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached). A large bore needle is then attached to the syringe, and the thread is intraperitoneally injected into a recipient in a minimal volume of the Lactated Ringer's Solution.

An alternative in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see T.C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection. Some disadvantages (especially for gene therapy) associated with adenovirus gene delivery include: (i) very low efficiency integration into the host genome; (ii) existence in primarily episomal form; and (iii) the host immune response to the administered virus, precluding readministration of the adenoviral vector.

By deleting portions of the adenovirus genome, larger inserts (up to 7 kb) of heterologous DNA can be accommodated. These inserts may be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (i.e., the human 293 cell line). When intravenously administered to intact animals, adenovirus primarily targets the liver. If the adenoviral delivery system has an E1 gene deletion, the virus cannot replicate in the host cells. However, the host's tissue (i.e., liver) will express and process (and, if a signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see A. Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

As would be evident to one of ordinary skill in the art, polyclonal antibodies can be generated from inoculating a variety of warm-blooded animals such as horses, cows, goats, sheep, dogs, chickens, rabbits, mice, hamsters, guinea pigs and rats as well as transgenic animals such as transgenic sheep, cows, goats or pigs. Antibodies may also be expressed in yeast and fungi in modified forms as well as in mammalian and insect cells. The ZGCL-1 polypeptide or a fragment thereof serves as an antigen (immunogen) to inoculate an animal or elicit an immune response. Suitable antigens would include the ZGCL-1 polypeptide encoded by SEQ ID NO:2 from amino acid residue 1–479 of SEQ ID NO:2, or a contiguous 9–479 amino acid residue fragment thereof. The immunogenicity of a ZGCL-1 polypeptide may be increased through the use of an adjuvant, such as alum (aluminum hydroxide) or Freund's complete or incomplete adjuvant. Polypeptides useful for immunization also include fusion polypeptides, such as fusions of ZGCL-1 or a portion thereof with an immunoglobulin polypeptide or with an affinity tag. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization. Preferred peptides to use as antigens are hydrophilic peptides such as those predicted by one of skill in the art from a hydrophobicity plot, see for example, Hopp and Woods (*Proc. Nat. Acad. Sci. USA* 78:3824–8, 1981) and Kyte and Doolittle (*J. Mol. Biol.* 157: 105–142, 1982).

As used herein, the term "antibodies" includes polyclonal antibodies, affinity-purified polyclonal antibodies, monoclonal antibodies, and antigen-binding fragments thereof, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to ZGCL-1 protein or peptide, and selection of antibody display libraries in phage or similar vectors (for instance, through use of immobilized or labeled ZGCL-1 protein or peptide).

Antibodies are defined to be specifically binding if they bind to a ZGCL-1 polypeptide with a binding affinity ($K_a$) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The binding affinity of an antibody can be readily determined by one of ordinary skill in the art (for example, by Scatchard analysis).

Alternative techniques for generating or selecting antibodies useful herein include in vitro exposure of lymphocytes to ZGCL-1 protein or peptide, and selection of antibody display libraries in phage or similar vectors (for instance, through use of immobilized or labeled ZGCL-1 protein or peptide).

Genes encoding polypeptides having potential ZGCL-1 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the ZGCL-1 sequences disclosed herein to identify proteins which bind to ZGCL-1. These "binding proteins" which interact with ZGCL-1 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as ZGCL-1 "antagonists" to block ZGCL-1 binding and signal transduction in vitro and in vivo. These anti-ZGCL-1 binding proteins would be useful for inhibiting ZGCL-1 mediated activity.

A variety of assays known to those skilled in the art can be utilized to detect antibodies which specifically bind to ZGCL-1 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant ZGCL-1 protein or polypeptide.

Antibodies and binding proteins to ZGCL-1 may be used for tagging cells that express ZGCL-1; for isolating ZGCL-1 by affinity purification; for diagnostic assays for determining circulating levels of ZGCL-1 polypeptides; for detecting or quantitating soluble ZGCL-1 as marker of underlying pathology or disease; in analytical methods employing FACS; for screening expression libraries; for generating anti-idiotypic antibodies; and as neutralizing antibodies or as antagonists to block ZGCL-1 mediated activity both in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies and binding proteins herein may also be directly or indirectly conjugated to drugs, toxins, radionuclides and the like, and these conjugates used for in vivo diagnostic or therapeutic applications. Moreover, antibodies to ZGCL-1 or fragments thereof may be used in vitro to detect denatured ZGCL-1 or fragments thereof in assays, for example, Western Blots or other assays known in the art.

These antibodies and binding proteins would also be useful as contraceptives to prevent the fertilization of an egg. Such antibodies would act as antagonists by inhibiting a component(s) of spermatogenesis and/or sperm activation. Such antibody "antagonists" can be used for contraception in humans and animals, in particular, domestic animals and livestock. For instance, anti-ZGCL-1 immunization could be used in place of surgical forms of contraception (such as spaying and neutering) in animals, and would allow for the possibility of future breeding of those animals if desired.

ZGCL-1 ligand polypeptides may be used to identify and characterize genes which bind to ZGCL-1. Proteins and peptides of the present invention can be immobilized on a column and membrane preparations run over the column (*Immobilized Affinity Ligand Techniques*, Hermanson et al., eds., Academic Press, San Diego, Calif., 1992, 195–202). Proteins and peptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

The ZGCL-1 polynucleotides and/or polypeptides disclosed herein can be useful as therapeutics. Polypeptides of the present invention are used to stimulate proliferation or differentiation of testicular cells. Proliferation and differentiation can be measured using cultured testicular cells or in vivo by administering molecules of the present invention to the appropriate animal model. Cultured testicular cells include dolphin DB1.Tes cells (CRL-6258); mouse GC-1 spg cells (CRL-2053); TM3 cells (CRL-1714); TM4 cells (CRL-1715); and pig ST cells (CRL-1746), available from American Type Culture Collection, 12301 Parklawn Drive, Rockville, Md.

The initially identified EST was derived from a human heart tumor library. ZGCL-1 proteins and polypeptides may play a role in the development of cardiovasculature tissue, proliferation and differentiation of endothelial cells and cardiomyocytes. Proliferation can be measured using cultured cardiac cells or in vivo by administering molecules of the claimed invention to the appropriate animal model. Cultured cells include cardiac fibroblasts, cardiac myocytes, skeletal myocytes, human umbilical vein endothelial cells from primary cultures. Established cell lines include: NIH 3T3 fibroblast (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc. Natl. Acad. Sci.* 89:8928–89, 1992) and LNCap.FGC adenocarcinoma cells (ATCC No. CRL-1740.)

Assays measuring cell proliferation or differentiation are well known in the art. For example, assays measuring proliferation include such assays as chemosensitivity to neutral red dye (Cavanaugh et al., *Investigational New Drugs* 8:347–54, 1990), incorporation of radiolabelled nucleotides (Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–79, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–33, 1988). Assays measuring differentiation include, for example, measuring cell-surface markers associated with stage-specific expression of a tissue, enzymatic activity, functional activity or morphological changes (Watt, *FASEB*, 5:281–84, 1991; Francis, *Differentiation* 57:63–75, 1994; Raes, *Adv. Anim. Cell Biol. Technol. Bioprocesses*, 161–71, 1989).

In vivo assays for evaluating cardiac neogenesis or hyperplasia include treating neonatal and mature rats with the molecules of the present invention. The animals cardiac function is measured as heart rate, blood pressure, and cardiac output to determine left ventricular function. Postmortem methods for assessing cardiac improvement include: increased cardiac weight, nuclei/cytoplasmic volume, staining of cardiac histology sections to determine proliferating cell nuclear antigen (PCNA) vs. cytoplasmic actin levels (Quaini et al., *Circulation Res.* 75:1050–63, 1994 and Reiss et al., *Proc. Natl. Acad. Sci.* 93:8630–5, 1996).

In vivo assays for evaluating the effect of ZGCL-1 polypeptides on testes are also well known in the art. For example, compounds can be injected intraperitoneally for a specific time duration. After the treatment period, animals are sacrificed and testes removed and weighed. Testicles are homogenized and sperm head counts are made (Meistrich et al., *Exp. Cell Res.* 99:72–8, 1976).

Spermatogenesis is a sequential process and takes place in the seminiferous tubules, where germ cells ultimately mature into spermatozoa. Testis-specific factors that influence the maturation process may come directly from the Sertoli cells that are in contact with the sperm cells, or may be paracrine or endocrine factors. Many of the molecules produced outside the seminiferous tubules are transported into the sperm cell microenvironment by transport and binding proteins that are expressed by the Sertoli cells within the seminiferous tubules.

Paracrine factors that cross the cellular barrier and enter the sperm cell microenvironment include molecules secreted from Leydig cells. Leydig cells are located in the interstitial space found between the seminiferous tubules, and produce several factors believed to play an important role in the maturation process, such as testosterone, Leydig factor, IGF-1, inhibin and activin. The expression of these, and other factors, may be specific to a defined stage in the spermatogenic cycle.

The tissue specificity of ZGCL-1 expression suggests a role in spermatogenesis, and in view of this specificity, agonists and antagonists have enormous potential in both in vitro and in vivo applications. ZGCL-1 proteins and polypeptides and ZGCL-1 agonists are useful for stimulating proliferation and development of target cells in vitro and in vivo. For example, agonist compounds are useful as components of defined cell culture media, and may be used alone or in combination with cytokines and hormones to replace serum that is commonly used in cell culture. Agonists are thus useful in specifically promoting the growth and/or development of testis-derived cells in culture. Agonist compounds could be used to influence cellular differentiation, proliferation or development through up-regulation of ZGCL-1-modulated gene expression. Agonists and antagonists may also prove useful in the study of spermatogenesis and infertility. Antagonists are useful as research reagents for characterizing sites of DNA binding to the ZGCL-1 transcription factor. Antagonists are also useful for modulating ZGCL-1 mediation transcription. For example, ZGCL-1 antagonists may be useful as male contraceptive agents.

ZGCL-1 polypeptides and ZGCL-1 agonists would be useful therapeutics to treat infertility. Accordingly, proteins of the present invention may have applications in enhancing fertilization during assisted reproduction in humans and in animals. Such assisted reproduction methods are known in the art and include artificial insemination, in vitro fertilization, embryo transfer and gamete intrafallopian transfer, for example. Such methods are useful for assisting men and women who may have physiological or metabolic disorders that prevent natural conception. Such methods may also be used by women who are unable or do not desire to conceive naturally for other reasons. Such methods are also used in animal breeding programs, such as for livestock, zoological animal, endangered species or racehorse breeding and could be used as methods for the creation of transgenic animals. Proteins of the present invention can be added to expand the number of donor sperm cells prior fertilization of an egg. It is advantageous to increase the number of sperm during such procedures to enhance the likelihood of successful fertilization. The invention provides methods of enhancing fertilization during assisted reproduction wherein a mammalian ZGCL-1 polypeptide is combined with sperm prior to fertilization of the egg, or to an egg-sperm mixture. Within one embodiment the assisted reproduction is artificial insemination. Within another embodiment the assisted reproduction is in vitro fertilization.

Polypeptides of the present invention can used to enhance viability of cryopreserved sperm, in particular, to enhance the number of viable sperm upon thawing. Such cryopreserved sperm can be used in association with methods of assisted reproduction. The invention provides methods of enhancing viability of cryopreserved sperm for use in fertilization of an egg, wherein a mammalian ZGCL-1 polypeptide is added to sperm prior to fertilization, or to an egg-sperm mixture.

Fusion of the ZGCL-1 polypeptide and an affinity tag (e.g., Glu—Glu affinity tag, FLAG tag, maltose-binding protein, an immunoglobulin domain) may be used to select sperm at a particular developmental stage for use in in vitro fertilization procedures. Staging the sperm increases the number and type of desired sperm, thereby increasing the likelihood of successful fertilization.

In vivo, ZGCL-1 and ZGCL-1 agonists would find application in the treatment of infertility, in particular, male infertility. It is estimated that 5–6% of men of reproductive age are infertile and a predominant cause is abnormal sperm count. ZGCL-1 polypeptides and proteins can be administered to enhance sperm count. Expression vectors containing polynucleotides encoding ZGCL-1 polypeptides or proteins linked with a polynucleotide encoding a testis specific receptor can be administered for delivery to and expression in testis tissue. ZGCL-1 could also be packaged with a testis-specific receptor such that uptake of the ZGCL-1 polypeptides and proteins occurred only in the testis. Alternatively, ZGCL-1 proteins or polypeptides could be injected directly into the testis. The invention provides methods of treating infertility wherein a mammalian ZGCL-1 polypeptide is administered to enhance sperm count. In a related embodiment administration is in testicular tissue.

As used herein antagonists are molecules which either bind to ZGCL-1 polypeptides or, alternatively, to a gene to which ZGCL-1 polypeptides bind, thereby inhibiting or eliminating the function of ZGCL-1. Such ZGCL-1 antagonists would include antibodies; binding proteins; oligonucleotides which bind either to the ZGCL-1 polypeptide or to its associated gene(s); natural or synthetic analogs of ZGCL-1 polypeptides which retain the ability to bind specific genes but do not result in transcription. Such analogs could be peptides or peptide-like compounds. Natural or synthetic small molecules which bind to receptors of ZGCL-1 polypeptides and prevent transcription are also contemplated as antagonists.

These ZGCL-1 antagonists are useful agents in methods related to fertility and contraception by selectively intercepting a process(es) leading to successful reproduction. As such, ZGCL-1 antagonists would be useful for inhibiting spermatogenesis and sperm activation. Such ZGCL-1 antagonists can be used for contraception in humans and animals, in particular domestic animals and livestock, where they ultimately act to prevent the successful fertilization of an egg. Such antagonists could be used, for instance, in place of surgical forms of contraception (such as spaying and neutering), and would allow for the possibility of future breeding of treated animals, if desired, by discontinuing administration of the antagonist. ZGCL-1 antagonists may prove useful similar to progesterone antagonists. Antiprogestogens, which antagonize binding but do not activate, effectively block the action of progesterone and are used as contraceptive agents. The invention provides methods of contraception wherein an antagonist of a mammalian ZGCL-1 polypeptide as described above is administered to a male recipient to prevent fertilization of an egg. Within one embodiment the antagonist is an anti-ZGCL-1 binding protein. Within a related embodiment the antagonist is an anti-ZGCL-1 antibody.

The invention also provides isolated and purified ZGCL-1 polynucleotide probes. Such polynucleotide probes can be RNA or DNA. DNA can be either cDNA or genomic DNA. Polynucleotide probes are single or double-stranded DNA or RNA, generally synthetic oligonucleotides, but may be generated from cloned cDNA or genomic sequences and will generally comprise at least 16 nucleotides, more often from 17 nucleotides to 25 or more nucleotides, sometimes 40 to 60 nucleotides, and in some instances a substantial portion, domain or even the entire ZGCL-1 gene or cDNA. The synthetic oligonucleotides of the present invention have at least 80% identity to a representative ZGCL-1 DNA sequence (SEQ ID NO:1) or its complements. Preferred regions from which to construct probes include the 5' and/or 3' coding sequences, DNA binding domains, affinity domains, signal sequences and the like. Techniques for developing polynucleotide probes and hybridization techniques are known in the art, see for example, Ausubel et al., eds., *Current Protocols in Molecular Biology*, John Wiley and Sons, Inc., N.Y., 1991. For use as probes, the molecules can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

Such probes can also be used in hybridizations to detect the presence or quantify the amount of ZGCL-1 gene or mRNA transcript in a sample. ZGCL-1 polynucleotide probes could be used to hybridize to DNA or RNA targets for diagnostic purposes, using such techniques such as fluorescent in situ hybridization (FISH) or immunohistochemistry. Polynucleotide probes could be used to identify genes encoding ZGCL-1-like proteins. For example, ZGCL-1 polynucleotides can be used as primers and/or templates in PCR reactions to identify other novel transcription factors. Such probes can also be used to screen libraries for related sequences encoding novel transcription factors. Such screening would be carried out under conditions of low stringency which would allow identification of sequences which are substantially homologous, but not requiring complete homology to the probe sequence. Such methods and conditions are well known in the art, see, for example, Sambrook et al., *Molecular Cloning: A Laboratory Manual*, Second Edition, Cold Spring Harbor, N.Y., 1989. Such low stringency conditions could include hybridization temperatures less than 42° C., formamide concentrations of less than 50% and moderate to low concentrations of salt. Libraries may be made of genomic DNA or cDNA. Polynucleotide probes are also useful for Southern, Northern, or slot blots, colony and plaque hybridization and in situ hybridization. Mixtures of different ZGCL-1 polynucleotide probes can be prepared which would increase sensitivity or the detection of low copy number targets, in screening systems.

ZGCL-1 polypeptides may be used within diagnostic systems. Antibodies or other agents that specifically bind to ZGCL-1 may be used to detect the presence of circulating polypeptides. Such detection methods are well known in the art and include, for example, enzyme-linked immunosorbent assay (ELISA) and radioimmunoassay. Immunohistochemically labeled antibodies can be used to detect ZGCL-1 in biological samples. ZGCL-1 levels can also be monitored by such methods as RT-PCR, where ZGCL-1 mRNA can be detected and quantified. Such methods could be used as diagnostic tools to monitor and quantify polypeptide levels. The information derived from such detection methods would provide insight into the significance of ZGCL-1 polypeptides in various conditions or diseases, and as a would serve as diagnostic methods for conditions or diseases for which altered levels of ZGCL-1 are significant. Altered levels of ZGCL-1 ligand polypeptides may be indicative of pathological conditions including cancer and cardiac and reproductive disorders.

The present invention also provides reagents which will find use in diagnostic applications. For example, the ZGCL-1 gene, a probe comprising ZGCL-1 DNA or RNA or a subsequence thereof can be used to determine if the ZGCL-1 gene is present on chromosome 5 or if a mutation has occurred. Detectable chromosomal aberrations at the ZGCL-1 gene locus include but are not limited to aneuploidy, gene copy number changes, insertions, deletions, restriction site changes and rearrangements.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA—RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

The invention also provides nucleic acid-based therapeutic treatment. If a mammal has a mutated or lacks a ZGCL-1 gene, the ZGCL-1 gene can be introduced into the cells of the mammal. In one embodiment, a gene encoding a ZGCL-1 polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes virus 1 (HSV1) vector (Kaplitt et al., *Molec. Cell. Neurosci*. 2:320–30, 1991), an attenuated adenovirus vector, such as the vector described by Stratford-Perricaudet et al. (*J. Clin. Invest*. 90:626–30, 1992), and a defective adeno-associated virus vector (Samulski et al., *J. Virol*. 61:3096–101, 1987; Samulski et al., *J. Virol*. 63:3822–28, 1989).

In another embodiment, the gene can be introduced in a retroviral vector, e.g., as described in Anderson et al., U.S. Pat. No. 5,399,346; Mann et al., *Cell* 33:153, 1983; Temin et al., U.S. Pat. No. 4,650,764; Temin et al., U.S. Pat. No. 4,980,289; Markowitz et al., *J. Virol*. 62:1120, 1988; Temin et al., U.S. Pat. No. 5,124,263; Dougherty et al., WIPO Publication WO 95/07358; and Kuo et al., Blood 82:845–52, 1993.

Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–17, 1987; and Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. It is clear that directing transfection to particular cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting. Targeted peptides, e.g., hormones or neurotransmitters, and proteins such as antibodies, or non-peptide molecules could be coupled to liposomes chemically.

It is possible to remove the cells from the body and introduce the vector as a naked DNA plasmid and then re-implant the transformed cells into the body. Naked DNA vector for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter (see, for example, Wu et al., *J. Biol. Chem*. 267:963–7, 1992; Wu et al., *J. Biol. Chem*. 263:14621–24, 1988).

The ZGCL-1 polypeptides are also contemplated for pharmaceutical use. Pharmaceutically effective amounts of ZGCL-1 polypeptides, agonists or ZGCL-1 antagonists of the present invention can be formulated with pharmaceutically acceptable carriers for parenteral, oral, nasal, rectal, topical, transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. Slow or extended-release delivery systems, including any of a number of biopolymers (biological-based systems), systems employing liposomes, and polymeric delivery systems, can also be utilized with the compositions described herein to provide a continuous or long-term source of the ZGCL-1 polypeptide or antagonist. Such slow release systems are applicable to formulations, for example, for oral, topical and parenteral use. The term "pharmaceutically acceptable carrier" refers to a carrier medium which does not interfere with the effectiveness of the biological activity of the active ingredients and which is not toxic to the host or patient. One skilled in the art may formulate the compounds of the present invention in an appropriate manner, and in accordance with accepted practices, such as those disclosed in Remington's Pharmaceutical Sciences, Gennaro (ed.), Mack Publishing Co., Easton, Pa. 1990.

As used herein a "pharmaceutically effective amount" of a ZGCL-1 polypeptide, agonist or antagonist is an amount sufficient to induce a desired biological result. The result can be alleviation of the signs, symptoms, or causes of a disease, or any other desired alteration of a biological system. For example, an effective amount of a ZGCL-1 polypeptide is that which provides either subjective relief of symptoms or an objectively identifiable improvement as noted by the clinician or other qualified observer. For example, such an effective amount of a ZGCL-1 polypeptide results in an increase in sperm count. Effective amounts of the ZGCL-1 polypeptides can vary widely depending on the disease or symptom to be treated. The amount of the polypeptide to be administered and its concentration in the formulations, depends upon the vehicle selected, route of administration, the potency of the particular polypeptide, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art. Typically a dose will be in the range of 0.1–100 mg/kg of subject. Doses for specific compounds may be determined from in vitro or ex vivo studies in combination with studies on experimental animals. Concentrations of compounds found to be effective in vitro or ex vivo provide guidance for animal studies, wherein doses are calculated to provide similar concentrations at the site of action.

The dosages of the present compounds used to practice the invention include dosages effective to result in the desired effects. Estimation of appropriate dosages effective for the individual patient is well within the skill of the ordinary prescribing physician or other appropriate health care practitioner. As a guide, the clinician can use conventionally available advice from a source such as the Physician's Desk Reference, 48$^{th}$ Edition, Medical Economics Data Production Co., Montvale, N.J. 07645–1742 (1994).

Preferably the compositions are presented for administration in unit dosage forms. The term "unit dosage form" refers to physically discrete units suitable as unitary dosed for human subjects and animals, each unit containing a predetermined quantity of active material calculated to produce a desired pharmaceutical effect in association with the required pharmaceutical diluent, carrier or vehicle. Examples of unit dosage forms include vials, ampules, tablets, caplets, pills, powders, granules, eyedrops, oral or ocular solutions or suspensions, ocular ointments, and oil-in-water emulsions. Means of preparation, formulation and administration are known to those of skill, see generally Remington: *The Science and Practice of Pharmacy*, Gennaro, ed., Mack Publishing Co., Easton, Pa., 19th ed., 1995.

The invention is further illustrated by the following non-limiting examples.

EXAMPLES

Example 1

Identification of ZGCL-1

Novel ZGCL-1 ligand-encoding polynucleotides and polypeptides of the present invention were initially identified by querying an EST database. An initial EST from a human heart tumor library was found. A second EST, from fetal mouse, was identified which was 87% identical at the nucleotide level to the human EST. Using this information, oligonucleotide primers ZC12991 (SEQ ID NO:5) and ZC12992 (SEQ ID NO:6) were made to the EST sequence and a pooled human testis library was screened using PCR. Eighty reactions were set up, each consisted of 2.5 µl 10X PCR reaction buffer (Boehringer Mannheim, Indianapolis, Ind.), 2 µl dNTPs mix (2.5 mM each, Perkin-Elmer, Foster City, Calif.), 0.5 µl sense primer, ZC 12,992 (20 pmol/µl), 0.5 µl antisense primer, ZC 12,991 (20 pmol/µl), 2.5 µl RediLoad (Research Genetics, Inc., Huntsville, Ala.), 0.5 µl AmpliTaq™ (Perkin-Elmer Cetus, Norwalk, Conn.) about 2–4 ng of DNA from an individual testis library pool and ddH$_2$O for a total volume of 25 µl. The reactions were overlaid with an equal amount of mineral oil and sealed. The PCR cycler conditions were as follows: an initial 35 cycles of a 20 second denaturation at 94° C., 30 second annealing at 55° C. and 30 second extension at 72° C., followed by a final 1 cycle extension of 10 minutes at 72° C. PCR products were analyzed on a 1% agarose gel and three pools giving the expected 200 bp PCR product were replated on to LB plates. Colonies were screened by PCR using gene-specific primers.

Four individual colonies were picked from each pool and added to microcentrifuge tubes by swirling the toothpick with the colony on it in a tube containing 18.5 µl H$_2$O, 2.5 µl 10× Taq polymerase buffer (Boehringer Mannheim, Indianapolis, Ind.), 2 µl 10 mM dNTPs (Perkin Elmer), 0.75 µl ZC12991 (SEQ ID NO:5) (20 pmol/µl), 0.75 ml ZC12992 (SEQ ID NO:6) (20 pmol/µl ), and 0.5 µl Taq polymerase. Amplification reactions were incubated at 94° C. for 1 minute to lyse the bacteria and expose the plasmid DNA, then run for 25 cycles of 94° C., 20 seconds; 55° C., 30 seconds; 72° C., 30 seconds to amplify cloned inserts, followed by a 10 minute extension at 72° C. Products were analyzed by electrophoresis on a 1% agarose gel. Clones giving a single 200 bp product were identified as positive, and the sequence confirmed by sequence analysis.

One clone, 83.1.3 was used to identify the corresponding cDNA. The clone was amplified using a QIAwell 8 plasmid kit (Qiagen, Inc., Chatsworth, Calif.) according to manufacturer's instructions, a 5 ml overnight culture in LB +50 mg/ml ampicillin was prepared. The template was sequenced on an Applied Biosystems™ model 373 DNA sequencer (Perkin-Elmer Cetus, Norwalk, Conn.) using the ABI PRISM™ Dye Terminator Cycle Sequencing Ready Reaction Kit (Perkin-Elmer Corp.) according the manufacturer's instructions. Oligonucleotides ZC694 (SEQ ID NO:7), ZC2681 (SEQ ID NO:8), ZC12991 (SEQ ID NO:5), ZC12992 (SEQ ID NO:6), ZC14122 (SEQ ID NO:9), ZC14183 (SEQ ID NO:10), ZC14184 (SEQ ID NO:11), ZC14237 (SEQ ID NO:12), ZC14238 (SEQ ID NO:13), ZC14284 (SEQ ID NO:14) and ZC14345 (SEQ ID NO:15) were used to sequence from the clone. Sequencing reactions were carried out in a Hybaid OmniGene Temperature Cycling System (National Labnet Co., Woodbridge, N.Y.). Sequencher 3.1 sequence analysis software (Gene Codes Corporation, Ann Arbor, Mich.) was used for data analysis. The resulting 1,467 bp sequence is disclosed in SEQ ID NO:1 which contained the initially identified EST sequence.

Example 2

Tissue Distribution

Human Multiple Tissue Northern Blots (MTN I, MTN II, and MTN III; Clontech) were probed with an approximately 200 bp (SEQ ID NO:16) PCR derived probe containing the sequence of the EST. The probe was amplified from a human heart Marathon™-ready cDNA library using oligonucleotide primers ZC12991 (SEQ ID NO:5) and ZC12992 (SEQ ID NO:6). The Marathon™-ready cDNA library was prepared according to manufacturer's instructions (Marathon cDNA Amplification Kit; Clontech, Palo Alto, Calif.) using human heart poly A$^+$ RNA (Clontech). The probe was amplified in a polymerase chain reaction as follows: 35 cycles of 94° C. for 20 seconds, 55° C. for 30 seconds, and 72° C. for 30 seconds, followed by 1 cycle at 72° C. for 10 minutes. The resulting DNA fragment was electrophoresed on a 2% GTG agarose gel, the fragment was purified using the QIAquick™ method (Qiagen, Chatsworth, Calif.), and the sequence was confirmed by sequence analysis. The probe was radioactively labeled using the random priming MULTIPRIME DNA labeling system (Amersham, Arlington Heights, Ill.), according to the manufacturer's specifications. The probe was purified using a NUCTRAP push column (Stratagene, La Jolla, Calif.). ExpressHyb™ (Clontech) solution was used for prehybridization and as a hybridizing solution for the Northern blots. Hybridization took place overnight at 65° C. using 1×10$^6$ cpm/ml of labeled probe. The blots were then washed at 50° C. in 0.1×SSC, 0.1% SDS. A predominant transcript of 3.2 kb was detected in testis. Reduced expression was seen in thyroid, spinal cord, stomach, lymph node and trachea. A weak transcript was seen in placenta and pancreas at 4.5 kb.

Example 3

Chromosomal Assignment and Placement of ZGCL-1

ZGCL-1 was mapped to chromosome 5 using the commercially available version of the Whitehead Institute/MIT Center for Genome Research's GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of ZGCL-1 with the GeneBridge 4 RH Panel, 25 µl reactions were set up in a PCRable 96-well microtiter plate (Stratagene, La Jolla, Calif.) and used in a RoboCycler Gradient 96 thermal cycler (Stratagene). Each of the 95 PCR reactions consisted of 2.5 µl 10× KlenTaq reaction buffer (Clontech), 2 µl dNTPs mix (2.5 mM each, Perkin-Elmer), 1.25 µl sense primer, ZC 12992 (SEQ ID NO:6), 1.25 µl antisense primer, ZC 12991 (SEQ ID NO:5), 2.5 µl RediLoad (Research Genetics), 0.5 µl 50× Advantage KlenTaq Polymerase Mix (Clontech), 25 ng of DNA from an individual hybrid clone or control and ddH$_2$O for a total volume of 25 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 58° C. and 1 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that ZGCL-1 maps 10.09 cR from the framework marker WI-6737 on the chromosome 5 WICCR radiation hybrid map. Relative to the centromere, its nearest proximal marker was WI-4897 and its nearest distal maker was WI-14295. The use of surrounding markers position ZGCL-1 in the 5q35.3 region on the integrated LDB chromosome 5 map (The Genetic Location Database, University of Southampton, WWW server:http://cedar.genetics.soton.ac.uk/public_html/).

Genes mapping to human chromosome 5q34–q35 have been primarily localized to mouse chromosome 11, in the A5-B1 and A1-B1 region. The mouse "germ cell deficient" gene, GCD, locus maps to chromosome 11 in the A2-A3 region (Duncan et al., *Mamm. Genome* 6:697–9, 1995). Germ cell deficient leads to improper migration and/or proliferation of primordial germ cells during embryonic development resulting in infertility in the adult mouse. Mice having this mutation have been hypothesized to be animal models for the human reproductive disorders, premature ovarian failure and Sertoli cell only syndrome.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprising amino acid residues 1–478 of SEQ ID NO:2.

2. An isolated polypeptide according to claim 1, covalently linked amino terminally or carboxy terminally to a moiety selected from the group consisting of affinity tags, toxins, radionucleotides, enzymes and fluorophores.

* * * * *

SEQUENCE LISTING

<160> NUMBER OF SEQ ID NOS: 16

<210> SEQ ID NO 1
<211> LENGTH: 1469
<212> TYPE: DNA
<213> ORGANISM: homo sapiens
<220> FEATURE:
<221> NAME/KEY: CDS
<222> LOCATION: (34)...(1469)

<400> SEQUENCE: 1

```
ggggctcggc ccggaggccg gacactggag acg atg cgg cgg gcc acg gat tct        54
                                   Met Arg Arg Ala Thr Asp Ser
                                    1               5 gtt act gtg cgg ggc agc cac aag cgc aag cgg agc agc ggg tcc ttc       102
Val Thr Val Arg Gly Ser His Lys Arg Lys Arg Ser Ser Gly Ser Phe
         10                  15                  20 tgc tac tgt cac cct gac tcg gag acg gac gag gat gag gag gag ggg       150
Cys Tyr Cys His Pro Asp Ser Glu Thr Asp Glu Asp Glu Glu Glu Gly
     25                  30                  35 gac gag cag cag cgg ctc ctc aac acc cct cga agg aaa aaa tta aag       198
Asp Glu Gln Gln Arg Leu Leu Asn Thr Pro Arg Arg Lys Lys Leu Lys
 40                  45                  50                  55 agt aca tct aaa tat att tat caa aca tta ttt ttg aat ggt gaa aac       246
Ser Thr Ser Lys Tyr Ile Tyr Gln Thr Leu Phe Leu Asn Gly Glu Asn
                 60                  65                  70 agt gac att aag att tgt gct cta gga gaa gaa tgg agc tta cac aaa       294
Ser Asp Ile Lys Ile Cys Ala Leu Gly Glu Glu Trp Ser Leu His Lys
             75                  80                  85 ata tat tta tgt caa tct ggc tac ttt tct agt atg ttc agt ggt tct       342
Ile Tyr Leu Cys Gln Ser Gly Tyr Phe Ser Ser Met Phe Ser Gly Ser
         90                  95                 100
```

-continued

| | |
|---|---|
| tgg aaa gaa tcc agc atg aat att att gaa ctg gag att cct gac cag<br>Trp Lys Glu Ser Ser Met Asn Ile Ile Glu Leu Glu Ile Pro Asp Gln<br>105                                 110                        115 | 390 |
| aac att gat gta gaa gca ctg cag gtt gca ttt ggt tca ctg tat cga<br>Asn Ile Asp Val Glu Ala Leu Gln Val Ala Phe Gly Ser Leu Tyr Arg<br>120                       125                   130                   135 | 438 |
| gat gat gtc ttg ata aag ccc agt cga gtt gtt gcc att ttg gca gca<br>Asp Asp Val Leu Ile Lys Pro Ser Arg Val Val Ala Ile Leu Ala Ala<br>                 140                   145                   150 | 486 |
| gct tgt ttg ctg cag ttg gac ggt tta ata cag cag tgt ggt gag aca<br>Ala Cys Leu Leu Gln Leu Asp Gly Leu Ile Gln Gln Cys Gly Glu Thr<br>         155                   160                   165 | 534 |
| atg aag gaa aca gtt aat gtg aaa act gta tgt ggc tat tac aca tca<br>Met Lys Glu Thr Val Asn Val Lys Thr Val Cys Gly Tyr Tyr Thr Ser<br>        170                   175                  180 | 582 |
| gca ggg acc tat gga tta gat tct gta aag aaa aag tgc ctt gaa tgg<br>Ala Gly Thr Tyr Gly Leu Asp Ser Val Lys Lys Lys Cys Leu Glu Trp<br>185                                 190                       195 | 630 |
| ctt cta aac aat ttg atg act cac cag aat gtt gaa ctt ttt aaa gaa<br>Leu Leu Asn Asn Leu Met Thr His Gln Asn Val Glu Leu Phe Lys Glu<br>200                                 205                   210                   215 | 678 |
| ctc agt ata aat gtc atg aaa cag ctc att ggt tca tct aac tta ttt<br>Leu Ser Ile Asn Val Met Lys Gln Leu Ile Gly Ser Ser Asn Leu Phe<br>        220                   225                  230 | 726 |
| gtg atg caa gtg gag atg gat ata tac act gct cta aaa aag tgg atg<br>Val Met Gln Val Glu Met Asp Ile Tyr Thr Ala Leu Lys Lys Trp Met<br>         235                   240                   245 | 774 |
| ttc ctt caa ctt gtg cct tct tgg aat gga tct tta aaa cag ctt ttg<br>Phe Leu Gln Leu Val Pro Ser Trp Asn Gly Ser Leu Lys Gln Leu Leu<br>        250                   255                  260 | 822 |
| aca gaa aca gat gtc tgg ttt tct aaa cag agg aaa gat ttt gaa ggt<br>Thr Glu Thr Asp Val Trp Phe Ser Lys Gln Arg Lys Asp Phe Glu Gly<br>265                                 270                   275 | 870 |
| atg gcc ttt ctt gaa act gaa caa gga aaa cca ttt gtg tca gta ttc<br>Met Ala Phe Leu Glu Thr Glu Gln Gly Lys Pro Phe Val Ser Val Phe<br>280                                 285                   290                   295 | 918 |
| aga cat tta agg tta caa tat att atc agt gat ctg gct tct gca aga<br>Arg His Leu Arg Leu Gln Tyr Ile Ile Ser Asp Leu Ala Ser Ala Arg<br>                 300                   305                   310 | 966 |
| att att gaa caa gat gct gta gta cct tca gaa tgg ctc tct tct gtg<br>Ile Ile Glu Gln Asp Ala Val Val Pro Ser Glu Trp Leu Ser Ser Val<br>               315                   320                   325 | 1014 |
| tat aaa cag cag tgg ttt gct atg ctg cgg gca gaa cag gac agt gag<br>Tyr Lys Gln Gln Trp Phe Ala Met Leu Arg Ala Glu Gln Asp Ser Glu<br>330                                 335                   340 | 1062 |
| gtg ggg cct caa gaa atc aat aaa gaa gaa cta gag gga aac agc atg<br>Val Gly Pro Gln Glu Ile Asn Lys Glu Glu Leu Glu Gly Asn Ser Met<br>345                                 350                   355 | 1110 |
| agg tgt ggt aga aag ctt gcc aaa gat ggt gaa tac tgc tgg cgt tgg<br>Arg Cys Gly Arg Lys Leu Ala Lys Asp Gly Glu Tyr Cys Trp Arg Trp<br>360                                 365                   370                   375 | 1158 |
| aca ggt ttt aac ttc ggc ttc gac cta ctt gta act tac acc aat cga<br>Thr Gly Phe Asn Phe Gly Phe Asp Leu Leu Val Thr Tyr Thr Asn Arg<br>                 380                   385                   390 | 1206 |
| tac atc att ttc aaa cgc aat aca ctg aat cag cca tgt agc gga tct<br>Tyr Ile Ile Phe Lys Arg Asn Thr Leu Asn Gln Pro Cys Ser Gly Ser<br>               395                   400                   405 | 1254 |
| gtc agt tta cag cct cga agg agc ata gca ttt aga tta cgt ttg gct<br>Val Ser Leu Gln Pro Arg Arg Ser Ile Ala Phe Arg Leu Arg Leu Ala<br>410                                 415                   420 | 1302 |

-continued

```
tct ttt gat agt agt gga aaa cta ata tgt agt aga aca act ggc tat    1350
Ser Phe Asp Ser Ser Gly Lys Leu Ile Cys Ser Arg Thr Thr Gly Tyr
    425                 430                 435 caa ata ctt aca ctt gaa aag gat cag gaa caa gtg gtg atg aac ttg    1398
Gln Ile Leu Thr Leu Glu Lys Asp Gln Glu Gln Val Val Met Asn Leu
440                 445                 450                 455 gac agc agg ctt ctg atc ttc cct tta tat atc tgc tgt aac ttc ttg    1446
Asp Ser Arg Leu Leu Ile Phe Pro Leu Tyr Ile Cys Cys Asn Phe Leu
                460                 465                 470 tat ata tca cca gaa aaa aag aa                                     1469
Tyr Ile Ser Pro Glu Lys Lys
            475

<210> SEQ ID NO 2
<211> LENGTH: 478
<212> TYPE: PRT
<213> ORGANISM: homo sapiens

<400> SEQUENCE: 2

Met Arg Arg Ala Thr Asp Ser Val Thr Val Arg Gly Ser His Lys Arg
1               5                   10                  15

Lys Arg Ser Ser Gly Ser Phe Cys Tyr Cys His Pro Asp Ser Glu Thr
            20                  25                  30

Asp Glu Asp Glu Glu Gly Asp Glu Gln Gln Arg Leu Leu Asn Thr
        35                  40                  45

Pro Arg Arg Lys Lys Leu Lys Ser Thr Ser Lys Tyr Ile Tyr Gln Thr
    50                  55                  60

Leu Phe Leu Asn Gly Glu Asn Ser Asp Ile Lys Ile Cys Ala Leu Gly
65                  70                  75                  80

Glu Glu Trp Ser Leu His Lys Ile Tyr Leu Cys Gln Ser Gly Tyr Phe
                85                  90                  95

Ser Ser Met Phe Ser Gly Ser Trp Lys Glu Ser Ser Met Asn Ile Ile
            100                 105                 110

Glu Leu Glu Ile Pro Asp Gln Asn Ile Asp Val Glu Ala Leu Gln Val
        115                 120                 125

Ala Phe Gly Ser Leu Tyr Arg Asp Asp Val Leu Ile Lys Pro Ser Arg
    130                 135                 140

Val Val Ala Ile Leu Ala Ala Cys Leu Leu Gln Leu Asp Gly Leu
145                 150                 155                 160

Ile Gln Gln Cys Gly Glu Thr Met Lys Glu Thr Val Asn Val Lys Thr
                165                 170                 175

Val Cys Gly Tyr Tyr Thr Ser Ala Gly Thr Tyr Gly Leu Asp Ser Val
            180                 185                 190

Lys Lys Lys Cys Leu Glu Trp Leu Leu Asn Asn Leu Met Thr His Gln
        195                 200                 205

Asn Val Glu Leu Phe Lys Glu Leu Ser Ile Asn Val Met Lys Gln Leu
    210                 215                 220

Ile Gly Ser Ser Asn Leu Phe Val Met Gln Val Glu Met Asp Ile Tyr
225                 230                 235                 240

Thr Ala Leu Lys Lys Trp Met Phe Leu Gln Leu Val Pro Ser Trp Asn
                245                 250                 255

Gly Ser Leu Lys Gln Leu Leu Thr Glu Thr Asp Val Trp Phe Ser Lys
            260                 265                 270

Gln Arg Lys Asp Phe Glu Gly Met Ala Phe Leu Glu Thr Glu Gln Gly
        275                 280                 285
```

```
Lys Pro Phe Val Ser Val Phe Arg His Leu Arg Leu Gln Tyr Ile Ile
    290                 295                 300

Ser Asp Leu Ala Ser Ala Arg Ile Ile Glu Gln Asp Ala Val Val Pro
305                 310                 315                 320

Ser Glu Trp Leu Ser Ser Val Tyr Lys Gln Gln Trp Phe Ala Met Leu
                325                 330                 335

Arg Ala Glu Gln Asp Ser Glu Val Gly Pro Gln Glu Ile Asn Lys Glu
            340                 345                 350

Glu Leu Glu Gly Asn Ser Met Arg Cys Gly Arg Lys Leu Ala Lys Asp
        355                 360                 365

Gly Glu Tyr Cys Trp Arg Trp Thr Gly Phe Asn Phe Gly Phe Asp Leu
    370                 375                 380

Leu Val Thr Tyr Thr Asn Arg Tyr Ile Ile Phe Lys Arg Asn Thr Leu
385                 390                 395                 400

Asn Gln Pro Cys Ser Gly Ser Val Ser Leu Gln Pro Arg Arg Ser Ile
                405                 410                 415

Ala Phe Arg Leu Arg Leu Ala Ser Phe Asp Ser Ser Gly Lys Leu Ile
            420                 425                 430

Cys Ser Arg Thr Thr Gly Tyr Gln Ile Leu Thr Leu Glu Lys Asp Gln
        435                 440                 445

Glu Gln Val Val Met Asn Leu Asp Ser Arg Leu Leu Ile Phe Pro Leu
    450                 455                 460

Tyr Ile Cys Cys Asn Phe Leu Tyr Ile Ser Pro Glu Lys Lys
465                 470                 475

<210> SEQ ID NO 3
<211> LENGTH: 569
<212> TYPE: PRT
<213> ORGANISM: Drosophila melanogaster

<400> SEQUENCE: 3

Met Gly Gln Ile Val Gly Ser Met His Met Asn Val Ala Glu Val Phe
1                   5                   10                  15

Ser Asn Arg Arg Lys Arg Lys Arg Ser Thr Asp Ser Ser Leu Gly Lys
                20                  25                  30

Asp Asp Pro Ala Gln Leu Asp Thr Thr Gln Pro Lys Lys Lys Lys Leu
            35                  40                  45

Leu Thr Thr Thr Gln Tyr Ile Tyr Lys Ala Leu Phe Lys Glu Glu Lys
        50                  55                  60

Asn Ser Asp Val Ala Val Met Ala Leu Asp Lys Val Trp His Leu His
65                  70                  75                  80

Lys Val Tyr Leu Ser Gln Ser Pro Tyr Phe Tyr Thr Met Phe Asn Gly
                85                  90                  95

Thr Trp Arg Glu Ala Gln Gln Asn Phe Ile Gln Ile Thr Ile Leu Asp
                100                 105                 110

Asp Arg Ile Thr Val Ala Ser Leu Asp Ala Val Phe Gly Ser Met Tyr
            115                 120                 125

Ser Asp Glu Ile Glu Ile Glu Ser Ala Asp Val Ile Ser Val Leu Ala
        130                 135                 140

Thr Ala Thr Leu Phe His Leu Asp Gly Ile Ile Asp Lys Cys Ala Glu
145                 150                 155                 160

Val Met Val Asp Asn Ile Ser Pro Glu Thr Ala Ile Gln Tyr Tyr Glu
                165                 170                 175

Ala Ala Cys Gln Tyr Gly Val Val Gly Val Lys Lys Ser Thr Phe Gln
            180                 185                 190
```

-continued

```
Trp Phe Gln Ile Asn Leu Leu Ser Ile Tyr Ser Lys Gln Pro Asn Leu
            195                 200                 205

Leu Arg His Ile Ser Ile Glu Leu Met Ser Ala Leu Thr Ala Ser Pro
210                 215                 220

Asp Leu Tyr Val Met Gln Thr Glu Phe Ser Leu Tyr Thr Leu Leu Arg
225                 230                 235                 240

Thr Trp Met Phe Leu Arg Leu His Pro Asp Tyr Asp Pro Glu Asp Pro
            245                 250                 255

Val Gln Arg Ala Glu Ala Leu Lys Thr Gln Glu Leu Leu Val Asn Ala
            260                 265                 270

Gly Val Glu Thr His Ala Pro Ser Gly Asp Val Val Gln Trp Thr Tyr
            275                 280                 285

Phe Thr Ser Arg Ser Glu Glu Arg Ser Phe Leu Ala Thr Pro Glu Gly
            290                 295                 300

Gln Pro Tyr Val Lys Val Phe Gln Lys Leu Arg Thr Gln Tyr Leu Thr
305                 310                 315                 320

Asn His Tyr Met Asp Leu Lys Ile Ile Tyr Asn Asp Asn Ile Ile Pro
            325                 330                 335

Lys Glu Trp Leu Tyr Arg His Ile His Asn His Trp Asp Ala Leu Leu
            340                 345                 350

Arg Ile Asp His Gly Gln Glu Asp Cys Ser Pro Gln Gln Leu Asp Asp
            355                 360                 365

Glu Gln Phe Phe Glu Asn Cys Met Arg Cys Gly Arg Met Leu Leu Glu
            370                 375                 380

Pro Gly Tyr Gln Lys Trp Arg Trp Thr Gly Phe Asn Phe Gly Met Asp
385                 390                 395                 400

Leu Ile Leu Ile Met Asp Ser Arg Arg Leu Asn Ile Arg Arg His His
                405                 410                 415

Arg His Glu His Glu Arg Val Leu Ser Leu Gln Thr Lys Arg Lys Phe
            420                 425                 430

Met Val Arg Thr Thr Val Thr Ser Ile Asn Ala Gln Arg Gln Ala Val
            435                 440                 445

Phe Thr Gln Thr Ser Glu Ile Cys Ser Leu Ser Leu Glu Lys Asn Glu
450                 455                 460

Glu Val Pro Leu Met Val Leu Asp Pro Lys Leu Val His Pro Leu Leu
465                 470                 475                 480

Ile Ser Ile Asn Met Leu Val Val Met Pro Pro Asn Gln Ser Phe Lys
            485                 490                 495

Glu Ile Val Pro Leu Ser Glu Glu Ala Thr Thr Ser Leu Ser Ile Pro
            500                 505                 510

Ile Ser Glu Ile Gly Ala Asn Ser Asp Arg Pro Leu Ser Pro Ser Ser
            515                 520                 525

Ala Asp Asp Ser Ala Val Phe Ile Gly Asp Ser Glu Pro Ser Thr Pro
530                 535                 540

Ser Ser Pro Ala Pro Arg Pro Arg Ile Ala Trp Ser Ala Ser Glu Thr
545                 550                 555                 560

Gly Ala Ile Cys Gly Gln Leu Ala Cys
                565
```

<210> SEQ ID NO 4
<211> LENGTH: 1437
<212> TYPE: DNA
<213> ORGANISM: Artificial Sequence
<220> FEATURE:

-continued

```
<223> OTHER INFORMATION: Degenerate nucleotide sequence encoding ZGCL-1
      polypeptide of SEQ ID NO:2
<221> NAME/KEY: variation
<222> LOCATION: (1)...(1437)
<223> OTHER INFORMATION: Each N is independently A, T, G, or C.

<400> SEQUENCE: 4
atgmgnmgng cnacngayws ngtnacngtn mgnggnwsnc ayaarmgnaa rmgnwsnwsn     60
ggnwsnttyt gytaytgyca yccngaywsn garacngayg argaygarga rgarggngay    120
garcarcarm gnytnytnaa yacnccnmgn mgnaaraary tnaarwsnac nwsnaartay    180
athtaycara cnytnttyyt naayggngar aaywsngaya thaarathtg ygcnytnggn    240
gargartggw snytncayaa rathtayytn tgycarwsng gntayttyws nwsnatgtty    300
wsnggnwsnt ggaargarws nwsnatgaay athathgary tngarathcc ngaycaraay    360
athgaygtng argcnytnca rgtngcntty ggnwsnytnt aymgngayga ygtnytnath    420
aarccnwsnm gngtngtngc nathytngcn gcngcntgyy tnytncaryt ngayggnytn    480
athcarcart gyggngarac natgaargar acngtnaayg tnaaracngt ntgyggntay    540
tayacnwsng cnggnacnta yggnytngay wsngtnaara araartgyyt ngartggytn    600
ytnaayaayy tnatgacnca ycaraaygtn garytnttya argarytnws nathaaygtn    660
atgaarcary tnathggnws nwsnaayytn ttygtnatgc argtngarat ggayathtay    720
acngcnytna araartggat gttyytncar ytngtnccnw sntggaaygg nwsnytnaar    780
carytnytna cngaracnga ygtntggtty wsnaarcarm gnaargaytt ygarggnatg    840
gcnttyytng aracngarca rggnaarccn ttygtnwsng tnttymgnca yytnmgnytn    900
cartayatha thwsngayyt ngcnwsngcn mgnathathg arcargaygc ngtngtnccn    960
wsngartggy tnwsnwsngt ntayaarcar cartggttyg cnatgytnmg ngcngarcar   1020
gaywsngarg tnggnccnca rgarathaay aargargary tngarggnaa ywsnatgmgn   1080
tgyggnmgna arytngcnaa rgayggngar taytgytggm gntggacngg nttyaaytty   1140
ggnttygayy tnytngtnac ntayacnaay mgntayatha thttyaarmg naayacnytn   1200
aaycarccnt gywsnggnws ngtnwsnytn carccnmgnm gnwsnathgc nttymgnytn   1260
mgnytngcnw snttygayws nwsnggnaar ytnathtgyw snmgnacnac nggntaycar   1320
athytnacny tngaraarga ycargarcar gtngtnatga ayytngayws nmgnytnytn   1380
athttyccny tntayathtg ytgyaaytty ytntayathw snccngaraa raaraar      1437

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide ZC12991

<400> SEQUENCE: 5
ctgctgtatt aaaccgtcca actg                                             24

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide ZC12992

<400> SEQUENCE: 6
ctagtatgtt cagtggttct tgaa                                             24
```

```
<210> SEQ ID NO 7
<211> LENGTH: 20
<212> TYPE: DNA
<213> ORGANISM: Artificial Sequence
<220> FEATURE:
<223> OTHER INFORMATION: Oligonucleotide ZC694

<400> SEQUENCE: 7
taatacgact cactataggg                                               20

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide ZC1681

<400> SEQUENCE: 8
gaataagagt atagaaga                                                 18

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide ZC14122

<400> SEQUENCE: 9
cagtattcag acatttaacc                                               20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide ZC14183

<400> SEQUENCE: 10
gaaggtacta cagcatcttg                                               20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide ZC14184

<400> SEQUENCE: 11
aagtggtgat gaacttggac                                               20

<210> SEQ ID NO 12
<211> LENGTH: 20
<212> TYPE: DNA
<213> ORGANISM: Artificial Sequence
<220> FEATURE:
<223> OTHER INFORMATION: Olinucleotide ZC14237

<400> SEQUENCE: 12
gagatcgcac cattgcactc                                               20

<210> SEQ ID NO 13
<211> LENGTH: 20
<212> TYPE: DNA
<213> ORGANISM: Artificial Sequence
<220> FEATURE:
```

```
<223> OTHER INFORMATION: Oligonucleotide ZC14238

<400> SEQUENCE: 13
gctactgttt ccaactgatc                                                    20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide ZC14284

<400> SEQUENCE: 14
gtgcgatctc ggctcactgc                                                    20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide ZC14345

<400> SEQUENCE: 15
atgtcgtctt ggagatcggg                                                    20

<210> SEQ ID NO 16
<211> LENGTH: 200
<212> TYPE: DNA
<213> ORGANISM: Artificial Sequence
<220> FEATURE:
<223> OTHER INFORMATION: Northern probe

<400> SEQUENCE: 16
ctagtatgtt cagtggttct tggaaagaat ccagcatgaa tattattgaa ctggagattc        60
ctgaccagaa cattgatgta gaagcactgc aggttgcatt tggttcactg tatcgagatg       120
atgtcttgat aaagcccagt cgagttgttg ccattttggc agcagcttgt ttgctgcagt       180
tggacggttt aatacagcag                                                   200
```